(12) United States Patent
Bova

(10) Patent No.: US 6,316,234 B1
(45) Date of Patent: Nov. 13, 2001

(54) LASER CELL PURIFICATION SYSTEM

(76) Inventor: G. Steven Bova, 331 Tuscany Rd., Baltimore, MD (US) 21210

( * ) Notice: Subject to any disclaimer, the term of this patent is extended or adjusted under 35 U.S.C. 154(b) by 0 days.

(21) Appl. No.: 09/429,317

(22) Filed: Oct. 28, 1999

Related U.S. Application Data

(62) Division of application No. 08/530,791, filed on Sep. 19, 1995, now Pat. No. 6,040,139.

(51) Int. Cl.$^7$ .............................. C12N 13/00; A01N 1/00; C12M 1/36
(52) U.S. Cl. ................................ 435/173.7; 435/173.1; 435/286.2; 435/173.9; 435/1.1; 435/325; 435/284.1
(58) Field of Search ....................... 435/325, 1.1, 173.1, 435/173.7, 173.9, 284.1, 286.2

(56) References Cited

U.S. PATENT DOCUMENTS

| | | |
|---|---|---|
| 4,395,397 | 7/1983 | Shapiro . |
| 4,624,915 | 11/1986 | Schindler et al. . |
| 4,629,687 * | 12/1986 | Schindler et al. .................. 435/4 |
| 4,737,628 | 4/1988 | Lovoi . |
| 4,741,043 * | 4/1988 | Bacus ...................................... 382/6 |
| 4,785,806 | 11/1988 | Deckelbaum . |
| 4,785,815 | 11/1988 | Cohen . |
| 4,902,132 | 2/1990 | Murphy, Jr. et al. . |
| 5,098,426 * | 3/1992 | Sklar et al. ............................. 606/5 |
| 5,158,889 | 10/1992 | Hirako et al. . |
| 5,272,081 | 12/1993 | Weinreb et al. . |
| 5,352,613 * | 10/1994 | Tafas et al. ............................ 436/63 |
| 5,364,744 | 11/1994 | Buican et al. . |
| 5,374,556 | 12/1994 | Bennett et al. . |
| 5,843,644 | 12/1998 | Liotta et al. . |
| 5,843,657 | 12/1998 | Liotta et al. . |
| 5,874,266 * | 2/1999 | Palsson . |

FOREIGN PATENT DOCUMENTS

| | | |
|---|---|---|
| 4300698 | 7/1994 | (DE) . |
| 95/23960 | 8/1995 | (WO) . |

OTHER PUBLICATIONS

Copy of International Search Report from PCT/US96/14985, filed Sep. 18, 1996.
Downloaded material—source: http.//www.arctur.com. –45 pages.
Marchevsky et al., "Computerized Interactive Morphometry as a Potentially Useful Tool in the Classification of Non–Hodgkin's Lymphomas," Cancer, vol. 57, pp. 1544–1549, Apr. 15, 1986.*
Hadano et al., "Laser Microdissection and Single Unique Primer PCR Allow Generation of Regional Chromosome DNA CLones from a Single Human Chromosome," Genomics, vol. 11, pp. 364–373, 1991.*
F. Klimek et al., Carcinogenesis, vol. 5, No. 2, pp. 265–268 (1984).
D. Koppel, Biophys. J., vol. 28, pp. 281–291 (Nov. 1979).
Y. Kubo et al., Cancer Research, vol. 55, pp. 989–990 (Mar. 1995).
D. Shibata et al., American Journal of Pathology, vol. 141, No. 3, pp. 539–543 (Sep. 1992).

* cited by examiner

Primary Examiner—Christopher R. Tate
Assistant Examiner—Randall Winston
(74) Attorney, Agent, or Firm—Rothwell, Figg, Ernst & Manbeck

(57) ABSTRACT

A process and apparatus for cell purification and ablation is disclosed. The present invention comprises a laser system which directs radiant energy at computer or manually selected individual cells thereby disrupting DNA, RNA and protein structure in those cells. The present invention produces a purified tissue section containing relatively intact DNA, RNA or protein from only the untreated cells. This purified sample is suitable for amplification of material by PCR or other techniques for the analysis of molecular genetic features in the selected cells of interest.

8 Claims, 5 Drawing Sheets

LASER CELL PURIFICATION SYSTEM

CROSS REFERENCE TO RELATED APPLICATION

This application is a division of Ser. No. 08/530,791, filed Sep. 19, 1995, now U.S. Pat. No. 6,040,139.

BACKGROUND OF THE INVENTION

1. Field of the Invention

The invention involves a novel method and apparatus for obtaining pure cell populations or cell constituents such as DNA, RNA or proteins from target cells in tissue sections using ultraviolet (UV) laser-assisted ablation of non-target cells.

2. Description of the Background Art

Cancer is a leading cause of death in the United States. Treatments for cancers include surgery, chemotherapy, and radiation therapy, which cause considerable morbidity and often are ineffective. Standard pathological grading and staging cannot predict the susceptibility of a particular tumor to eradication by chemotherapy, radiation therapy, or other therapy, and thus many patients with solid tumors receive ineffective toxic therapy. Better prognostic indicators and therapeutic targets are needed for cancer treatment.

A large worldwide effort is underway to develop improved prognostic and therapeutic tools for cancer. New molecular biology techniques permit investigation of specific genetic alterations in cancers. Evidence is accumulating that information about specific DNA alterations in tumors, which predict cancer behavior, may provide important new tools for cancer diagnosis, prognosis, and therapy.

For example, a recent study found that in one of the most common cancers in children (Wilms' tumor), tumor-specific loss of heterozygosity of chromosome 16q predicts adverse outcome independent of histological type. Based on this knowledge, the subgroup of Wilms' tumor patients with favorable histology and loss of heterozygosity for chromosome 16q in their tumors may now benefit from earlier, more aggressive therapy. Further, in colon cancer, the status of chromosome 18q has recently been shown to have strong prognostic value in patients with cancer extending through the bowel without lymph node metastasis (stage II). Thus, stage II colon cancer patients with tumor specific loss of heterozygosity on chromosome 18q are a newly defined subset of patients that may benefit from more aggressive adjuvant therapy at the time of their initial diagnosis.

Other types of tumor-specific genetic alterations, including amplification of specific alleles and inactivation of specific genes or alleles by cytidine methylation have shown promise for providing important new prognostic information. It may be possible to define the "signature" of genetic lesions in an individual patient's tumor, permitting therapy tailored specifically to the genetic defects of the tumor.

Current molecular biologic techniques allow the study of DNA, RNA, and protein contained within cells. Some techniques allow cells to be studied in situ, with labelled molecular probes visualized under a microscope. These techniques are very useful, but currently are quite limited in their resolution and consistency. Other more powerful techniques for studying cellular DNA, RNA or protein depend on pooling of material from one or several cells. Studies based on such pooling have identified the first known gene-specific changes associated with cancer and other diseases, and have provided insight into the molecular processes involved in the transformation of cells from normal to abnormal.

Understanding molecular genetic changes involved in the pathogenesis of organ dysfunction requires studying groups of diseased cells in isolation and comparing them to phenotypically normal cells. The difficulty is that diseased cells in any tissue are usually accompanied by many phenotypically normal cells. Thus molecular studies reported to date have been limited to tissues in which the concentration of diseased cells is relatively high, such as in large, concentrated tumor masses. Various researchers have attempted to obtain purer samples of DNA, RNA, or protein from diseased cells by scraping portions of tissue sections away with a cutting instrument or by inking target areas of tissue sections and later exposing the section to UV light to destroy non-inked DNA and RNA.

Ultraviolet irradiation of such tissue has been found to cause single and double stranded DNA breaks, DNA crosslinks, generation of local denatured sites in DNA and DNA base destruction. Thus, it is known that ultraviolet irradiation of a tissue section can massively disrupt the DNA strand (as well as RNA and protein) contained within that tissue section. For example, selective UV irradiation (non-laser) exposure of portions of tissue sections was achieved by Shibata et al. (Amer. J. Pathol. 141(3):539–543, 1992) by covering target areas of stained tissue sections with black ink and UV irradiating the entire tissue sample with a standard broad spectrum UV light bulb. Shibata demonstrated that DNA within cells covered with the black ink is preserved, while DNA in UV exposed adjacent portions of the tissue was destroyed. This crude technique is markedly limited by the width of the black marking pen used, by difficulty in directing the pen to the desired location, and by the need to continually replace the pen in order to avoid contamination of inked areas by cellular material from areas previously inked. Another limitation is that inking must be performed while no cover slip is in place, markedly reducing optical resolution and making visual identification of cells nearly impossible in many cases.

Formalin fixed, paraffin embedded (FFPE) tissues are the basis for current pathology practice. They are readily available to most pathologists and cancer researchers and provide histological detail that remains the benchmark for pathology. FFPE tissue is not ideal for many molecular methods because DNA and RNA contained within this tissue is partially degraded. Although it is more difficult to isolate DNA of adequate quality for analysis from FFPE tissue sections than from unfixed, unembedded tissue, a number of studies have demonstrated that amplification of DNA fragments as long as 536 base pairs can be accomplished with tissue fixed in buffered formalin. However, the duration of storage, fixative used, fixation time, fixation temperature, and extraction procedures all affect the quality of DNA that can be isolated from paraffin. Recent molecular techniques have allowed a wide range of genetic alterations to be detected in DNA and RNA isolated from archival tissues. Most of these techniques are based on Polymerase Chain Reaction ("PCR").

PCR based genetic analysis of single cells or groups of cells has been used to discover molecular alterations in cells. For example, PCR techniques have been used to detect loss of heterozygosity, genomic DNA mutation, mitochondrial DNA mutation, DNA methylation, gene dosage, gene rearrangements, clonality and detection of DNA adducts. However, because cancer cells grow in close relation to noncancerous cells in all tissues, it is nearly impossible using heretofore known techniques to obtain pure tumor DNA. Hence, background signals from noncancerous cells often distort the analysis of genetic changes in tumors. For example, when a mutation is not detected in a particular gene in DNA isolated from a tumor, it is quite possible that the nonmutated sequence came from noncancerous cells' DNA contaminating the sample. This contamination problem was demonstrated in a controversy concerning the importance of the recently identified gene p16/MTS1. One of the gene's discoverers cast doubt on analyses of certain DNA samples which did not show p16 mutations because of contamination by noncancerous DNA.

The problem of background noise created by contaminating noncancerous cells was again emphasized by difficulty in identifying mutations in the breast cancer associated gene BRCA1 in sporadic and hereditary tumors. In cases of hereditary tumors, the individual inherits one mutated copy of the gene. Researchers have had difficulty studying the remaining copy of the gene in hereditary tumor samples because of background noise from contaminating normal cells, making it difficult to ascertain the frequency of specific BRCA1 genetic alterations. Because of the difficulty of obtaining pure breast cancer DNA samples in general, it is not known with confidence that in fact BRCA1 mutations are rare in non-hereditary breast tumors. Interpretation of results based on impure tissue samples are ambiguous in direct proportion to the degree of impurity of the DNA, RNA or protein isolated.

Current techniques of DNA, RNA and protein isolation and purification illustrate the problem of sample purity in researching genetic alterations in cancer.

For example, serial cryostat sectioning and trimming of frozen tumor-bearing tissue has been used to produce limited purification of tumor DNA and has been useful in the definition of loss of heterozygosity and other genetic alterations. Unfortunately, this cryostat-based "fractionation" of cancer tissue has a number of drawbacks. For example, most common primary tumors, including breast, ovarian, pancreatic, prostate cancers and others, are highly infiltrated with noncancerous cells. Hence, it is difficult to obtain better than 70% purity in the majority of cases using cryostat sectioning alone, since only relatively large regions of the tissue can be carved manually from the tissue block. Further, histological detail is often poor in frozen sectioned material, making interpretation difficult. In addition, cryostat methods cannot be applied easily to the clinical setting because clinicians find it inconvenient to freeze biopsy samples, and pathologists prefer paraffin embedded material for interpretation.

Improved signal (cancerous DNA) to noise (noncancerous DNA) ratio in PCR based allelic loss analysis has been achieved by mechanical microdissection of individual tissue sections or by a combination of broadband ultraviolet light treatment of the section after covering desired areas with black ink, followed by mechanical removal of the tissue from the slide. However, these manual microdissection methods have several drawbacks. For example, microdissection or ink-dotting must be performed without a cover slip in place which markedly reduces optical resolution. Further, manual dissection or ink dotting only allows the selective isolation of clumps of cells.

Microdissection using stage-mounted micromanipulators has been reported, but the lack of resolution without a coverslip in place typically precludes isolation of single cells. Moreover, the microdissection and ink-dotting techniques are extremely time-consuming and cumbersome.

In situ hybridization is another method of locating specific base sequences in tissue sections. For example, fluorescence in situ hybridization (FISH) has been used to show sequence deletions and ploidy anomalies in prostate tumors. However, in situ methods have several disadvantages. For example, genetic material in the section is consumed by the process and is not available for multiple analyses. In addition, the specificity of individual FISH probes is highly variable. Finally, many molecular alterations (mutations, methylation, small deletions, etc.) are not detectable with FISH.

Non-histological methods for enrichment of tissue samples of tumor cells are also possible, such as separation of ovarian tumor cells using flow cytometry, and enrichment of breast and prostate tumor cells with an avidin affinity column. However, these techniques are significantly limited because they require a tumor specific antibody, which is not available for the majority of tumors. Moreover, even if tumor specific antibodies were available for all tumors, use in a clinical setting would require separate separation protocols and columns for every tumor type, which would be very inefficient. Furthermore, specific antibodies are notoriously variable in their staining characteristics. Finally, these "blind" separation methods make it difficult to obtain both histological grading and molecular diagnostic information on the same tissue sample. Histological grading of tumors is one of the most powerful prognostic tools available and any new molecular analysis will be compared to standard histological grading techniques to determine their prognostic value, a comparison that will not easily be achieved with flow cytometry based or affinity column based purification systems. A method that combines the ability to obtain maximum enrichment of tumor cells while maintaining histological analysis of the sample has significant advantages over flow cytometry or column-based separation methods.

U.S. Pat. No. 5,272,081 discloses a method for selecting and separating individual cells in a sample for diagnostic purposes. In accordance with this method, cells are first separated, trapped in sized holes on a grid, each with a known location, and subjected to tests for selection. Once the cells on the grid have been tested and selected, the desired cells may be removed from the grid by selectively changing the electrical potential of conductors on the grid, or the undesired cells may be killed to effect separation. A major disadvantage of this method is that the cells must be suspended before they are trapped on the grid for testing. Cells in a standard paraffin embedded tissue sample, such as a biopsy sample, cannot be readily kept intact and separated by this method. Again, standard histological analysis of the same sample would be impossible, and usually the entire sample would be consumed by one experiment.

Also, U.S. Pat. Nos. 4,624,915 and 4,626,687 disclose methods and devices for the separation and segregation of living cells using a focused radiant energy beam. In accordance with these methods, living, anchorage-dependent target cells are moved on a microscope stage in two dimensions while the laser beam is directed through the objective lens of the microscope at individual living cells, or at the film supporting the cells. The living cells are viewed on the slides with no cover slip and while nutritive cell medium is flowing over the cells. Selection is based on a cellular light response to an attenuated laser beam, and undesired cells are killed with radiant energy from a focused, high power laser beam. Living cell selection can be accomplished by computer analysis of the fluorescence pattern of the living cells.

Freeze-dried tissue sections have been microdissected using a laser after first storing coordinates to be dissected from a non-freeze dried adjacent section using a drawing tube (Klimek et al., Carcinogenesis: 5(2):265–268, 1984). Because the tissue sections to be microdissected must be freeze-dried at −40° C. and stored under vacuum at −45° C., because the tissue shrinks when it is freeze dried, and because the regions to be dissected must be indirectly identified through the use of a drawing tube, this method is also very cumbersome and limited in precision. It does not allow specific individual cellular localization and ablation.

None of the known techniques contemplated for use with biopsy tissue samples have been used to reliably examine and selectively destroy individual cells, individual cell nuclei, or DNA within individual cells. The known techniques make it nearly impossible to routinely study small tissue samples in which there are a large percentage of non-diseased cells that cannot be cut out or selectively inked. Prostate biopsies, for example, may contain small foci of adenocarcinoma measuring 1 mm in diameter or less, surrounded by lymphocytes, smooth muscle and benign prostate cells. In most cases, it is extremely tedious or impossible to selectively destroy the lymphocytes, smooth muscle cells, and benign prostate cells using available techniques. These limitations make it difficult to bring routine pathologic diagnosis to the molecular level, because most tissue biopsies cannot be effectively studied using currently available techniques.

Using current tumor DNA purification techniques, noise from contaminating noncancerous DNA makes interpretation of data difficult and sometimes impossible, confounding cancer research and diagnosis. Accordingly, there is a profound need for a reliable technique to obtain highly enriched samples of tumor DNA, RNA and protein. Such a technique would be widely used by pathologists in clinical practice, cancer researchers, and in fact, any investigator who needed to purify individual cells or groups of cells from a heterogeneous tissue, cancerous or noncancerous.

SUMMARY OF THE INVENTION

In accordance with the present invention, a novel laser purification method and apparatus is disclosed for obtaining pure cell populations from a tissue section having a heterogenous cell population. This method allows one to obtain a tissue section having a heterogeneous cell population which, after treatment, has relatively intact DNA, RNA or protein from only untreated cells. The invention comprises a microscope, a support stage for supporting the tissue section and a drive means for providing relative movement between the stage and the microscope in an x-y coordinate plane. A video camera is provided for scanning the tissue section and creating a mosaic of video images representing the tissue section. These high resolution video images are displayed on a video display. Target cells in the tissue section are microscopically identified using established morphological criteria or fluorescent tagged antibodies. In one embodiment, the operator inspects the video images representing the magnified tissue section displayed on the video display and manually selects the target cells to be destroyed or preserved utilizing a touch or light sensitive video display screen or cursor system. In another embodiment, the target cells of interest are automatically identified based upon an analysis of the video images by a computer. In this embodiment, the operator can verify the target cells identified by the computer and has the option of either selecting additional cells of interest or deselecting cells identified by the computer. After the manual or automatic identification and selection of the target cells, the computer automatically directs a laser to photoablate the DNA, RNA or protein in the contaminating cells so that the proportion of intact DNA and RNA from the target cells is markedly increased.

Further purification of the tissue section is achieved with the present invention by analyzing the cells not photoablated in the purification steps described above under a higher magnification, and repeating the photoablation process of the present invention. Purification, in accordance with one aspect of the present invention, means that the tissue section having a heterogenous cell population, after treatment, will contain relatively intact DNA, RNA or protein from only the untreated cells.

The present invention is automated by using image analysis hardware and software, with minimal operator intervention, thereby allowing the DNA or RNA in selected portions of the tissue section to be automatically ablated, while the nonselected cells' DNA or RNA will remain intact for subsequent analysis by PCR or other genetic methods.

Further, a greater degree of optical resolution is obtainable with the present invention over prior art systems since a UV transparent quartz cover slip can be used during operation of the viewing and laser devices.

DETAILED DESCRIPTION OF THE PREFERRED EMBODIMENTS

Figure 1:
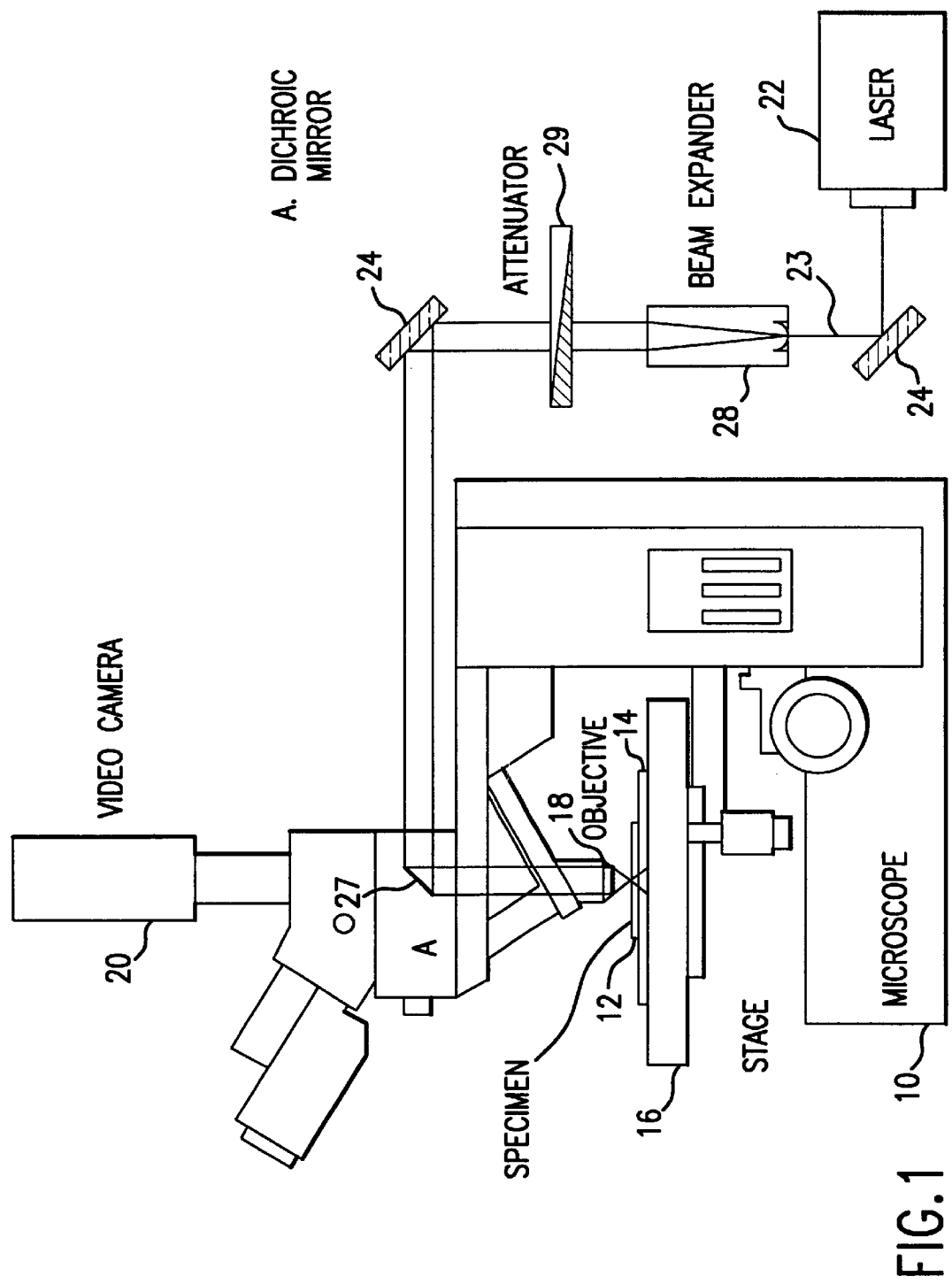
FIG. 1 is a schematic representation of the laser purification system in accordance with the present invention.
Figure 4:
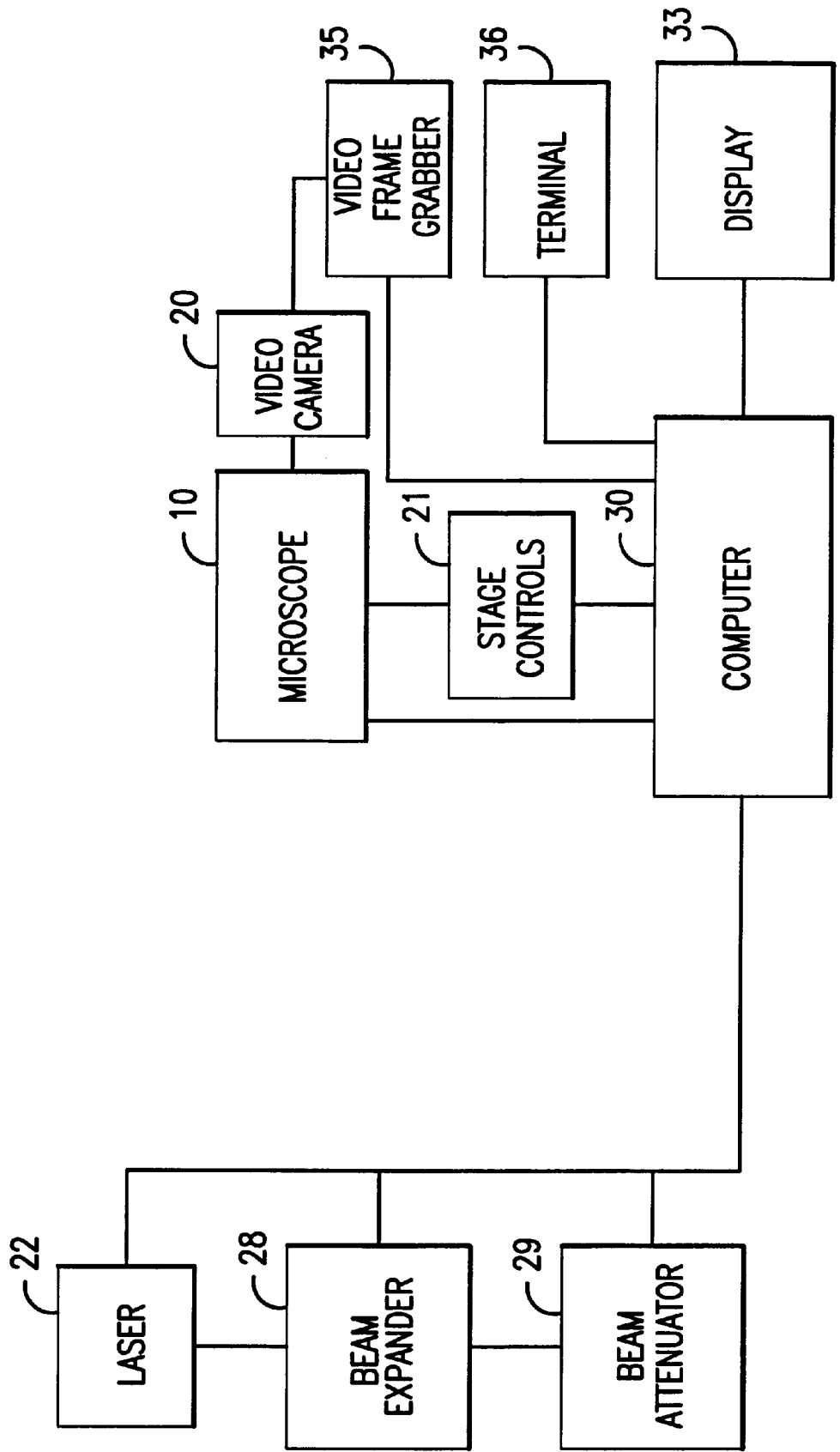
FIG. 4 is a block diagram illustrating the laser purification system in accordance with the present invention.

The laser purification system of the present invention is described in connection with FIGS. 1 and 4 which disclose a microscope 10 for viewing a tissue section 12 which contains a heterogenous population of cells, including target cells of interest, such as cancerous cells. The microscope 10 comprises an objective lens 18. The tissue section 12 is supported on a tissue support 14 which can be any suitable means for supporting a tissue section known to those skilled in the art, such as a slide. In one embodiment, the tissue support is a borosilicate glass slide.

Figure 2:
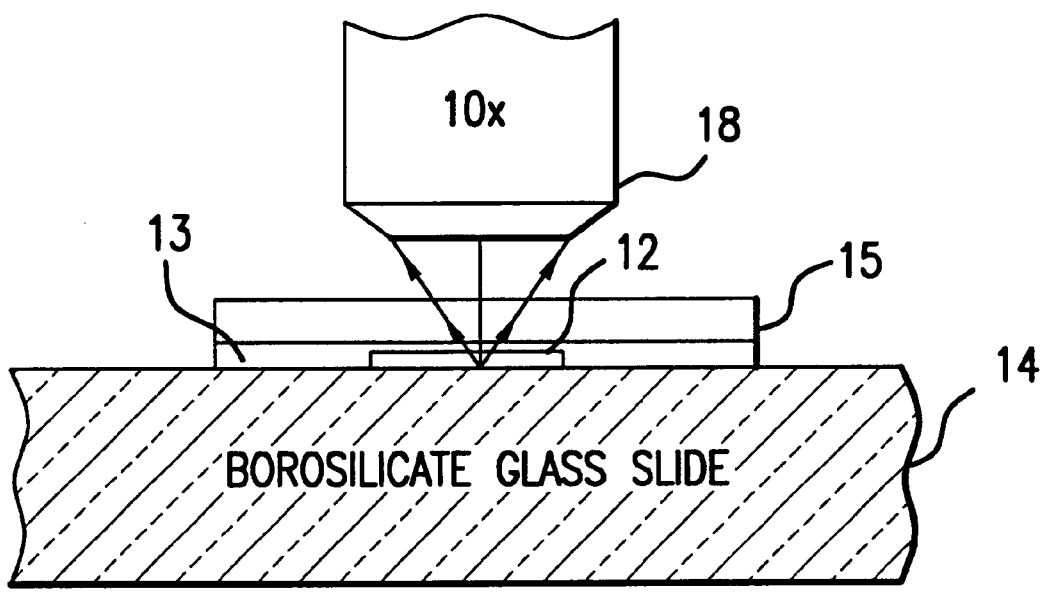
FIG. 2 is a schematic representation of the objective, quartz coverglass and tissue support of the laser purification system of FIG. 1.

In a preferred embodiment, a UV transparent quartz coverslip 15, as illustrated in FIG. 2, is placed between the tissue section 12 and the objective 18 which allows a greater degree of optical resolution. In one embodiment, the quartz coverslip 15 is approximately 0.15 mm to 0.25 mm thick or even thicker.

A suitable UV transmitting mounting medium 13 is placed between the coverslip 15 and the tissue section 12 and tissue support 14. Any mounting medium that allows at least partial UV light transmission, is clear (to allow good visualization), and does not interfere with later DNA, RNA, or protein recovery or analysis is suitable for use with this device. For example, one acceptable UV transparent mounting medium is sterile distilled water.

The tissue section 12 and tissue support 14 are removably mounted on a stage 16. The stage 16 comprises a drive means for providing relative movement between the stage 16 and the objective lens 18 in incremental locations in an x-y coordinate plane. The drive means also comprises means for generating an address signal within the x-y coordinate plane for each incremental location.

The drive means in accordance with the present invention can be any motorized stage known to those skilled in the art which provides controlled incremental movement of the stage and generates an address signal representing the incremental location. As illustrated in FIG. 4, the drive means includes stage controls 21 to control the movement of the stage 16 in response to address signals. In a preferred embodiment, the drive means is a motorized stage with computer interface. A motorized stage suitable for use with the present invention can be obtained by Ludl, Inc. such as, for example, a motorized stage having a resolution of approximately 0.1 um, repeatability of approximately 1 um, and accuracy of approximately 5 um. Of course, other motorized stages having greater or lesser accuracy, repeatability and resolution may be used as well.

The microscope 10 can be any suitable microscope known to those skilled in the art, such as an Olympus BX40 upright microscope. The Olympus BX40 microscope is an economical instrument with the key advantages of modular construction and infinity corrected optics, which eases the integration of the laser 22 to the microscope 10. Special UV transparent quartz objective lenses, such as those illustrated by objective 18, may be acquired from Optics for Research, Inc. or other suitable source.

As the tissue section is incrementally moved by drive means and stage 16, video camera 20 generates a video image of the tissue section at selected incremental locations in the x-y plane. In a preferred embodiment, the video camera 20 is mounted to microscope 10 as illustrated in FIG. 1. The signals generated by the video camera 20 representing each video image are input into a video frame grabber 35 which are then input into the computer 30, as illustrated in FIG. 4. The address signal of the stage 16 associated with each video frame are input into computer 30.

Image focus can be maintained manually by the operator by mechanically focussing the microscope 10. In a preferred embodiment, the image focus is maintained by automatic image focussing equipment which is well known to persons skilled in the art.

The video camera 20 can be any suitable color or monochrome video camera known to persons skilled in the art and is preferably a Sony XC-75 monochrome instrumentation camera or a high resolution color camera. In one embodiment of the present invention, the video camera 20 feeds up to 30 frames per second to the video frame grabber 35. The video frame grabber 35 can be any suitable video frame grabber known to persons skilled in the art and, in a preferred embodiment, is a Data Translation Quickcapture video frame grabber. Further, the computer 30 can be any suitable computer known to persons skilled in the art and, in a preferred embodiment, is a Apple PowerMac 8100 which has a 16 MB RAM and a 500 MB hard drive. A Pentium PC may also be used.

Figure 3:
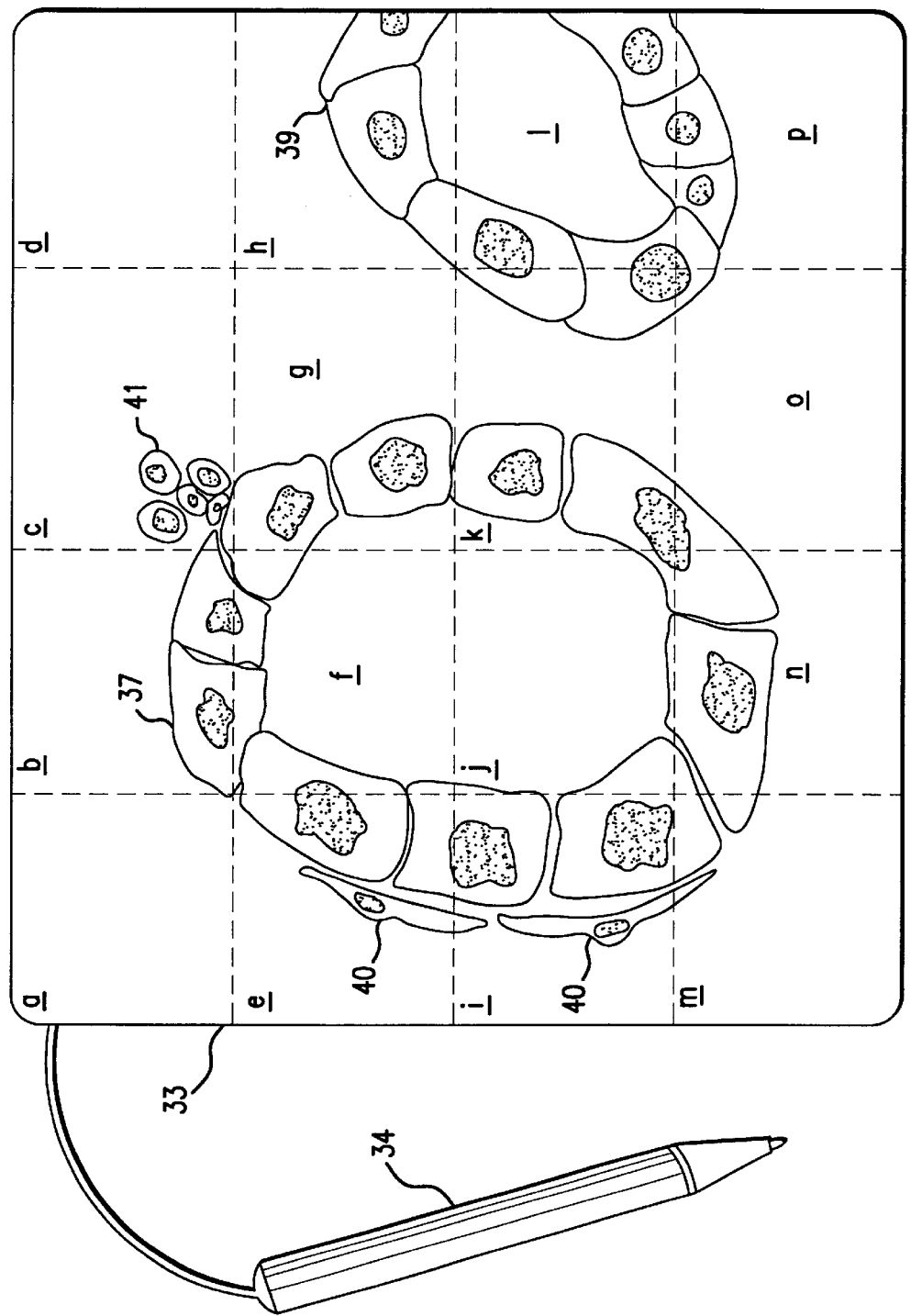
FIG. 3 is a schematic representation of the video display and the apparatus for manually selecting target cells from the tissue section in accordance with the present invention.

The present invention also comprises a selection means for selecting the target cells of interest from the heterogenous target tissue section 12. Selection is defined as choosing specific regions defined by specific x,y coordinates. In one embodiment, the selection means automatically selects the target cells of interest to be photoablated by a focussed radiant energy beam 23, as illustrated in FIG. 1. In accordance with this embodiment, the selection means comprises the computer 30 and a video display 33 which utilizes a light or touch sensitive screen, as illustrated in FIGS. 3 and 4. The computer 30 is programmed to analyze the video images from the video camera 20 and to identify target cells of interest based on various histological or biological characteristics or fluorescent characteristics of those cells selected by the operator. For example, the target cells could be identified using established morphological criteria or fluorescent tagged antibodies, as described below.

In another embodiment of the present invention, the selection means comprises a means for the manual selection of target cells of interest. In accordance with this embodiment, the computer 30 displays the video images generated by video camera 20 on a video display 33 (FIG. 3), creating a mosaic of the video images representing at least a portion of the entire tissue section. The operator then inspects the high resolution video images of the tissue section and manually selects target cells to be treated or target cells to be preserved. The manual selection of the target cells is accomplished in this embodiment by utilizing a touch or light sensitive screen in video monitor 33 or by using a cursor system or mouse. For example, the operator identifies the target cells of interest by tracing those cells using a light pen 34.

FIG. 3 illustrates a diagram representing a mosaic of high resolution video images representing a magnified tissue section containing a heterogenous population of cells, including non-cancerous cells and adenocarcinoma cells (gland forming cancer). The ring of gland forming cancer cells in this tissue section is represented by the numeral 37 and non-cancerous ring of prostate gland cells is represented by numeral 39. Further, noncancerous stromal cells are depicted as numeral 40 and non-cancerous lymphocytes are depicted as numeral 41. In this example, the operator can use the light pen 34 to outline the target cells of interest to be ablated, such as non-cancerous cells 39, 40 and 41. In accordance with the present invention, the operator can also elect to outline cells which are not to be ablated, such as by outlining the cancerous gland forming cells 37 in FIG. 3.

The computer identifies the specific address for each target cell of interest identified either automatically or manually by the operator.

After identification and selection of the target cells of interest, the present invention comprises a radiant energy beam generating means for automatically and selectively ablating only those target cells identified automatically or manually by the operator. Specifically, the radiant energy beam generating means automatically directs a radiant energy beam to photoablate the DNA, RNA or protein in the unwanted, contaminating cells. In a preferred embodiment, the radiant energy beam generating means generates an ultraviolet ("UV") laser beam 23 by UV laser 22.

The UV laser 22 can be any suitable laser known to those skilled in the art such as, for example, argon ion lasers, excimer pumped dye lasers, Nd:YAG lasers, KrF excimer lasers and XeCl lasers. In one embodiment the UV laser is a diode pumped solid state Nd:YLF laser which produces a collimated beam with a Gaussian intensity profile. The beam diameter can be any suitable beam diameter for causing photoablation of cells as is known to those skilled in the art. For example, the beam diameter can be any suitable diameter from less than approximately 1 micron to approximately 1 mm. In one embodiment, the beam diameter is approximately 10 um, which is the average diameter of human cell nuclei.

UV light is specifically selected for its known tendency to damage cellular DNA, RNA and protein. Laser light of any wavelength within the UV spectrum will be suitable for proper functioning of the present invention. UV laser light in the spectrum designated UV-C (200–290 nm) has the greatest potential for DNA, RNA and protein damage with the lowest energy applied and least heat production. Laser light with a wavelength above 290 nm could also be used, but may produce tissue boiling at lower energy levels.

The laser 22 can be controlled by the operator, through computer 30, to select the specific pulse duration, wavelength and energy level of the laser beam 23. In one embodiment, the laser 22 produces pulses having a duration of less than about 7 ns and no greater than 200 microJoules at 262 nm. In another embodiment, the laser 22 produces pulses at 248 nm. When the laser 22 is focused through a microscope objective to a spot of approximately 0.5 um diameter, the maximum optical power (fluence) exceeds 100 kiloJoules/cm$^2$ per pulse. The maximum fluence available is vastly greater than required, and fluence can be decreased to any level desired by the user. Conservative estimates suggest that organic materials such as biological tissues are completely ablated with 0.02 to 1 Joules/cm$^2$. Ceramics, glass and metals are ablated with 1 to 20 Joules/cm$^2$ The UV laser 22 is controlled by the computer 30, which issues command signals to initiate a burst of optical pulses 23. The laser output is brought to the laser port through a series of mirrors 24 and lenses, as illustrated in FIG. 1. A beam expander 28, controlled by the computer 30, is also provided so that laser beam spot size can be accurately and precisely controlled. The collimated and expanded UV laser beam 23 fills the back aperture of the objective lens 18, thus creating a diffraction-limited spot at the tissue section plane.

A dichroic mirror 27 is used at the position between the video camera 20 and the microscope objective lens 18, so that the tissue section can be viewed when the laser is active. The dichroic mirror 27 reflects light at wavelengths less than 300 nm (in one embodiment), but transmits visible light, protecting the operator from stray UV light at the eyepieces. Additional laser safety features include a keylock controlled power switch and a manual occluder at the laser output port. In one embodiment, a UV blocking swing-out shield is placed around the stage and contains a switch that will prevent laser firing while the shield is open.

The size of the laser spot at the tissue section depends on the diameter of the laser beam as it enters the optical train into the microscope 10. Beam expander 28 between the laser 22 and the microscope 10 allows the spot to be varied to increase or decrease the treatment area. The beam size can be selected by the operator and the computer 30 effectuates control of the beam size by controlling beam expander 28. The maximum treatment area is the field of view of the microscope 10 which depends on the numerical aperture of the objective lens in place. The minimum spot size obtainable depends on focal length of the objective lens. If the fluence used is sufficient only to produce inactivation of the target cells' RNA, DNA or protein in the target zone, the effect of scattered light will be minimized. Optimal laser fluence and exposure time will be determined by the user and will vary depending on the application (some tissues may requires higher UV doses to ablate DNA/RNA, for example).

The applied dose of UV radiation is controlled by the attenuator 29, varying the duration and number of pulses applied to the target zone, and varying the diameter of the spot. The operator can control these parameters by inputting the desired information into computer 30 through terminal 36 (FIG. 4) which controls the laser 22, beam expander 28 and beam attenuator 29.

The present invention utilizes any suitable quartz laser-to-microscope optics. For example, suitable quartz laser-to-microscope optics can be obtained from Microcosm, Inc. (a Maryland corporation). In one embodiment, the beam expander 28 and the laser 22 utilize serial interface electronics and software extensions to NIH-Image software (which is publicly available) to enable beam size and laser pulse trains to be computer controlled. In a preferred embodiment, the beam expander 28 is of Galilean design with variable magnification to control spot size. The magnification adjustment is motorized and controlled from the computer.

Operation of the Present Invention

The operation of the present invention will be described in connection with FIG. 5. An appropriately stained tissue section covered with a UV transparent quartz coverslip 15 is placed under the histologic microscope 10 with attached high resolution camera 20. The tissue section can be any suitable thickness known to persons skilled in the art such as, for example, a 6 micron thick section. The user selects the objective to be used (10×, 20×, 32× or 100× for example) and initiates the scanning function of the device. The tissue section then is moved in an x-y plane underneath the microscope by stage 16 and the drive means. The video camera 20 generates a video frame of each incremental portion of the tissue section as it is being scanned. After the entire tissue section is scanned, the system then presents the available images to the user. Because, in most cases, not all of the video images can be displayed on the video display 33 at once, the computer 30 divides the images into a number of non-overlapping visual fields. Each visual field constitutes a mosaic of video frames representing a portion of the tissue section of interest and is displayed on the video display 33. An example of a visual field is illustrated on FIG. 3. The operator can review all of the video fields until the entire region of interest has been reviewed.

In accordance with the present invention, the target cells which are to be either preserved or destroyed are identified using an automatic identification mode and/or a manual identification mode. In the automatic identification mode, the operator then sets the criteria by which the computer will automatically identify the target cells of interest to be ablated based on image characteristics. For example, the criteria for automatic identification of target cells are based on object color, hue, intensity, size, shape, texture, or any feature of combination of features definable by digitized image data.

The computer 30 then analyzes the video frames in accordance with the selection criteria and identifies cells falling within that selection criteria. The identified cells are contrasted from non-selected cells by any suitable manner such as by highlighting only those cells on video display 33. At this stage, the operator may check the computer selections to see if the target cells of interest have been properly identified for ablation. If the operator wants to identify additional cells to be ablated or deselect cells, the operator selects or deselects those cells by use, for example, of the light pen 34 on video display 33, as described below in connection with manual identification.

In the manual identification mode, the operator uses the displayed images to visually identify the target cells of interest using standard histomorphological criteria known to persons having skill in the art. A few examples of such target cells include identifiable cancer cells, identifiable muscle cells, or identifiable lymphocytes, etc., all of which have well known appearances to those knowledgeable in the art. Features of visual appearance which may be considered by the operator in either the manual or automatic identification mode are, for example, nuclear size, shape (e.g. roundness), texture and hue. The operator can also choose cells based on a combination of features, such as their visual appearance and their location in the tissue under study.

In the manual identification mode, the operator visually selects the target cells of interest by "coloring in", outlining or otherwise identifying those cells on the video monitor 33 using the light pen 34, illustrated in FIG. 3, or by using a mouse pointer, cursor system or touch sensitive system (not shown). For example, the operator may draw a circle to contain the single gland of cancer (37) contained in FIG. 3, and upon completing this circle, the software will automatically change the color of this circular region to indicate to the operator that it has been selected. The operator will be able then to erase or alter these selected regions as many times as necessary until the operator is satisfied with the selected regions.

When the operator is satisfied with the target cell selections in each of the images in the first visual field (from either the automatic or manual identification modes), the system immediately presents the second visual field to be viewed. When selections have been made for each image in each visual field, the operator can review the images in any or all visual fields. When the operator is satisfied with target cell selections from all of the images, the operator can then initiate the selective laser exposure process from the menu selections on display 33, utilizing terminal 36 (FIG. 4). The operator menu selections will contain choices such as, for example, fluence level, beam width, energy exposure per unit selected area, magnification level and whether to expose selected areas or expose non-selected areas. Before operating the system, these parameters will be set by the operator. After initial selection of laser treatment parameters, the operator will have the option of saving these settings for subsequent use as default settings, to further streamline the laser treatment process.

After the selected target cells of interest have been identified as discussed above, the computer 30 analyzes the data and calculates the course of motion for the motorized stage. As a preferred embodiment, to increase the speed of the photoablation process the software also analyzes the size of the regions to be photoablated, and where wide areas are to be ablated, the widest appropriate beam diameter is automatically applied based on the width of the area to be photoablated. The user then initiates a software-driven process whereby all of the selected cells are exposed to the UV laser automatically and unselected cells are left unexposed. Verification of accurate lasing can be accomplished in some cases by visible blanching of the tissue staining dye in areas exposed to the laser, with preservation of staining in non-lased areas. Laser fixation points made of UV sensitive ink can be placed on the slide as well, and can be used to verify accuracy. Appropriate shielding should be employed by the user to avoid exposure to the UV laser beam during use.

Figure 5:
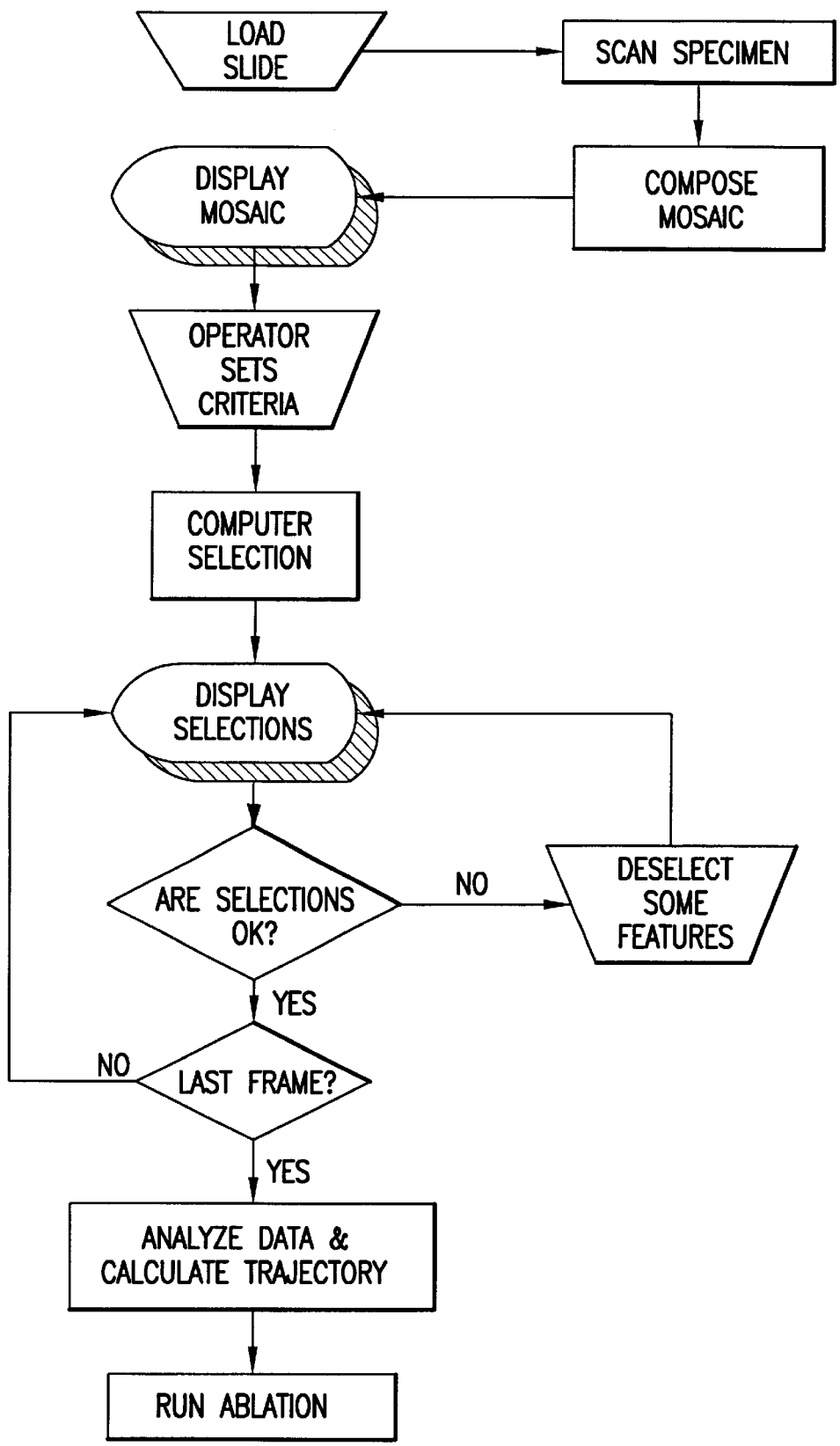
FIG. 5 is a flow chart illustrating the operation of the laser purification system in accordance with the present invention.

NIH-Image software, which is readily available, can be modified to provide a convenient, user-friendly selection and ablation protocol as described above and in accordance with the algorithm set forth in FIG. 5.

The operator may stop photoablation after completion of this stage or proceed to higher magnification to obtain greater sample purity, if desired and/or necessary. Based on visual estimation, tumors with tissue patterns consisting of concentrated clusters of cancer cells with a width of 100 um or more, surrounded by 50–500 micron wide acellular areas or noncancerous cells can be effectively concentrated using a lower power objective alone such as, for example, a 10× objective. One example of such a tissue is a lymph node containing focal cancer metastases. The total time required for photoablation up to this stage depends on the size of the tissue section examined, and the complexity of the selected regions. In the simplest case, for example a 1 cm diameter lymph node containing four 1 mm diameter metastatic foci, the process would take from 2–5 minutes. Selective photodissection of a breast or prostate needle biopsy containing focal carcinoma would take a similar amount of time.

If the operator wishes to further photodissect the areas left unexposed, the system is switched to a higher power objective lens such as, for example, a 20×, 32× or 100× lens, and the slide is re-scanned. Regions which have been exposed to the laser can be identified by their photobleached appearance, giving the operator visual confirmation of the effectiveness of photoablation and stage positioning. After scanning at the higher magnification, the system can again provide a tiled representation of these visual fields on the video display 33. The operator again chooses a mode of target selection, which will consist of either sequential viewing of each visual field and manually drawing the regions to be ablated, as described above, or by the use of the automatic identification mode. The operator then reviews the results of the automated selection and, if satisfied with those selections, begins photoablation of the regions selected.

If more convenient, the operator may identify nuclei to be preserved and instruct the system to destroy all other non-selected nuclei.

In one embodiment, when the operator desires to rescan the tissue section using a higher magnification, the operator can choose to scan only those portions of the tissue section that were not treated with the laser at the lower magnification. In this embodiment, the computer 30 recalls the coordinates of the regions photoablated in prior step and scans only regions of the tissue section that were not photoablated previously. In tissue section regions located on the edge of photoablated areas, the visual fields presented to the operator on video display 33 include a wide margin of previously photoablated tissue (such as, for example, a 50 $\mu$m margin) to avoid skipping areas.

After a purified tissue section is obtained using the apparatus and process described above, the tissue material can then be placed in an appropriate solution for molecular analysis. For example, the treated tissue section is removed from the slide upon which it is mounted using suitable means, such as a mechanical removal using a sterile scalpel, or by simple irrigation with appropriate buffer solution. The removed tissue is then placed in a suitable container such as a sterile microcentrifuge tube for molecular analysis.

The present invention enables accurate, efficient separation of contaminating cells from target cells of interest creating purified DNA, RNA or protein from tissue samples for molecular genetic analysis such as PCR.

The laser purification system of the present invention can be used with Brightfield microscopy. Brightfield microscopy employs a broad-spectrum or white light source for illumination of appropriately stained tissue sections. The light source is typically placed opposite the objective lens employed, with the tissue section to be examined placed between the microscope objective and the light source. Brightfield microscopy can be used with either the automatic or manual identification mode, i.e. it will allow the operator to visually select areas of interest in a semi-automated, interactive process based on image characteristics, as discussed above, or will permit the computer to automatically select target cells of interest, as described above.

One of many possible automated selection methods using Brightfield microscopy would involve the use of immunoperoxidase-stained tissue sections. Using immunoperoxidase staining, cells containing epitopes recognized by a specific antibody are typically stained brown. If a specific antibody is available for cells which the user wishes to selectively preserve or ablate within a tissue section, the entire selection process can be automated. For example, if the user wished to selectively study prostate epithelial cells within a tissue section, then the user could stain the tissue with a PSA-specific antibody using the immunoperoxidase technique, and stain all prostate epithelial cells brown (including both benign and malignant prostate cancer cells). The user then selects the scanning function, and after the tissue section has been scanned, then selects the "automated" submenu. From the automated submenu, the user would then choose criteria for object selection, as described above. In this case, the user can select "brown" and "edge detection" which would trigger the software to find the outer edges of any object colored brown and select this area. The user can review the selections made by the software prior to initiating the laser exposure process, as described above.

Another example of the operation of the present invention will be described in connection with using fluorescence microscopy. In fluorescence microscopy, cells are stained with a staining media which will fluoresce when illuminated by incident light, usually providing a bright signal on a dark background. The incident light used is an ultraviolet light source which excites fluorescent species within the staining medium. Specific wavelengths of light produced by the objects within the tissue can be examined by selection of filters which allow light of only defined spectra to pass.

Appropriate staining media will include, for example, propidium iodide which selectively stains DNA. Other media such as Fluorescein isothiocyanate (FITC), Rhodamine, or Texas Red labelled antibodies or newly developed more stable and intense fluorophore labels such as Cy3 or Cy5 (Amersham, Inc.) labelled antibodies (or other probes) may be used with this method.

An immunofluorescence based function will allow nearly fully automated photoablation, with the user simply monitoring the initial identification of target areas to be treated. The operator then directs the system to either photoablate the area containing fluorescent signal, or photoablate areas not containing fluorescent signal. The operator defines a fluorescence brightness threshold to determine the areas to be treated. Options for selection of target cells of interest using fluorescence microscopy will be identical to those for brightfield microscopy, including manual and automated identification methods. The automatic identification mode will operate similar to those used for immunoperoxidase staining described above, and will allow the user to review automated selections prior to selective laser treatment.

For example, the tissue section of interest is mounted on tissue support 14 and covered with the quartz coverslip 15 as described above. The operator selects filters appropriate for the fluorophore in use. The operator then views the tissue section with a low power objective such as, for example, 10× magnification, and prompts the system to scan the section and select targets based on signal intensity. The operator then reviews the selected targets field by field, and may decide to change the intensity threshold for targeting if too many or too few targets have been selected. Manual deselection or modification of targets in individual visual fields also is possible as described above. If target selection is not as precise as desired, the user may switch to a higher power objective and repeat the process. When appropriate intensity criteria for automatic target selection have been defined, based on review of some or all of the selections by the operator, the operator triggers the system to photoablate the selected regions. This process should take from 2–10 minutes for most sections using a 10× objective, longer if high power objectives are used.

After target cell selection, the selected regions will be indicated on the viewing screen either by a line circumscribing the region, or by a change in color or hue of the entire selected region, or by some combination of line and color or hue that can be chosen by the user. The user will accept, reject, or modify these selections. Processing speed will depend on the magnification used and the degree of selectivity desired.

Different combinations of coverslips and mounting media may be used. In one embodiment, a mildly UV absorbing mounting medium may be used to reduce laser scatter while allowing sufficient laser energy to reach the target. Tissue to be treated can be unfixed or fixed using any type of fixative known to persons skilled in the art such as, for example, formalin, alcohol or acetone.

If studying tumor cells' DNA only, as is often done, the operator may select or deselect targets based on whether or not the cells are cancerous by visual determination, as described above. Since only target nuclei need to be photoablated to produce selective DNA degradation, the histological patterns of growth and nuclear characteristics typical of many cancers should be recognizable with nuclear staining alone, staining with hematoxylin alone, or toluidine blue alone to increase image contrast and allow clear recognition of nuclear boundaries. Automated nuclear roundness determination using Brightfield microscopy could also be performed more easily in samples so prepared.

In another embodiment of the present invention, a beam expander is not used and the device can be configured to function with a fixed beam width, such as 10 um, or any other convenient beam width for the desired tissue or cells. Fixing at a diameter of 10 um should not interfere with cell-by-cell photodissection, since most mammalian cells are larger than 10 um in diameter, however operation at a fixed beam diameter will slow the photodissection process.

In still another embodiment, the present invention further comprises an image capture method and apparatus which enables the operator to select specific boundaries of the tissue section 12 to be scanned and treated, thereby significantly reducing time required to complete the overall laser purification process.

In accordance with the image capture process of the present invention, an appropriately stained tissue section 12 is covered with a UV transparent quartz coverslip 15 with suitable mounting media 13, as described above. The assembled slide, tissue section and coverslip is placed under the histologic microscope with attached high resolution camera 20. The operator selects the objective to be used which preferably is a low power magnification such as 2×, 4× or 10×. In one embodiment, the operator then uses a toggle switch 11 to move the motorized stage in the x,y plane such that the tissue section appears on the video monitor 33. The user then focuses the image on the video monitor 33 using the microscope focusing knob. In a preferred embodiment, the image is automatically kept in focus during the procedure through standard autofocus mechanisms known to those skilled in the art.

Viewing each visual field on the video display 33, the operator then identifies or marks specific boundaries of the tissue section to be scanned and treated. This may be performed manually by drawing a line using the mouse, light pen, touch screen, or cursor based system on the video monitor 33.

In another embodiment, the boundary identification can also be accomplished automatically by using the mouse, light pen, touch screen, or cursor based system to select an automatic scan function on the computer screen. Activating the automatic scan function causes the software to initiate movement of the stage in one direction. Using image analysis software, when the edge of the tissue section is reached, it is detected and the coordinates of the edge are stored in computer memory. The software then causes the stage to be moved and to identify and map the entire outer perimeter of the section using stage motion algorithms known in the art. The entire outer edge of the section is mapped in this fashion. Whether the edge is identified manually or automatically, the operator will have the option of displaying the shape of the outer perimeter of the section on the video screen 33 to help confirm that the entire section has been scanned. The software also calculates the number of captured images and corresponding number of visual fields needed to view the entire tissue section, and provides this information to the user on-screen.

Along with providing the user with the number of and visual fields needed to treat the selected portion of the tissue section or the entire tissue section, a menu of image capture options are provided on the video screen. The first option includes scanning and capturing images of the entire tissue section. These images are contiguous and mapped in the x,y plane by the software. The second option includes scanning and capturing images from only a portion of the tissue section selected by the operator. The third option includes scanning an initial portion of the section if adequate computer memory is not available. Target selection and laser treatment of this initial area must then be completed before the computer automatically reenters the image capture sequence for the next region. This is repeated until the entire section is treated.

In one embodiment, if the operator wishes to treat only specified portions of the section, the user chooses this option on the menu and selects an objective having a low magnification such as, for example, 2× or 4×. The software then triggers the motorized stage to quickly capture contiguous low resolution images of the entire section. The tiled images representing the entire tissue section are presented in one or more visual fields on the video display 33, depending on the size of the tissue section. The operator then uses a mouse, light pen, touch screen or cursor system to select the tiles to be treated. After this selection is made, the software prompts the user to capture images from the selected tiles at resolution adequate for target selection, which will be determined by the user's preferences and needs. The target selection and laser treatment are then carried out in accordance with the present invention, as described above.

Using the image capture process of the present invention allows for greater control over scanning and treatment functions which can greatly expedite the laser purification process of the present invention.

In still another embodiment of the present invention, a manual method and apparatus for purifying a tissue section by ablating the DNA, RNA or protein of unwanted cells is disclosed which is more economical (but more time consuming). In accordance with this embodiment, the UV laser can be mounted on a standard microscope with motorized or purely manual mechanical microcontrol of beam direction. The tissue section, which can comprise living and/or non-living cells, are supported by tissue support 14 and are covered by quartz coverslip 15. Under direct vision (through the microscope) while wearing UV protective goggles, the user applies the laser beam to the areas desired. Areas lased are identified as areas where the dye used to stain the tissue has blanched. To prepare the lased tissue for analysis, the quartz coverslip is removed manually, and the portion of tissue to be analyzed is physically removed from the slide using a sterile scalpel or scissors and placed in an appropriate reaction tube. The tissue is then placed in a buffer appropriate to the analysis desired.

An automated calibration system for the motorized stage can be used to measure the precision of the stage motion system to allow for correction of potential stage motion inaccuracies. In one such method, the surface of a test slide can be marked with the laser at high power, with a diffraction limited 5 micron diameter spot at a position with coordinates x1, y1. The stage will then be moved repeatedly away from x1, y1 to a fixed position x2, y2 and back to x1, y1. The position of the optical axis in relation x1, y1 will be measured by the image analysis system after each excursion using a cross hair in the viewing path as the reference point. This process may be repeated as many times as necessary to acquire a large data set for statistical analysis. Displacement from x1, y1 to x2, y2 can be varied to test whether precision varies with displacement. Stage motion is considered to be highly reproducible if there is an average of less than a two micron displacement of the optical axis after 10 excursions. If stage motion is highly reproducible as defined above, scanning and user-directed image processing of the entire tissue section (including multiple images) could be performed in a single step, followed by photoablation of selected areas in a second step. If stage motion is not highly reproducible as defined above, in order to avoid photoablation of unselected regions due to imprecise positioning, photoablation can be performed after regions to be ablated are selected from each image, minimizing the number of excursions from the optical axis between the time of image capture and photoablation.

A beam width control test routine also may be included which directs the system to produce beams of varying diameters such as, for example, 1, 10, 20, 40, and 100 um in diameter in rows on a glass slide. Fluence levels adequate to etch glass are used initially. Spot sizes are measured and analyzed by image analysis for mean values, roundness, and coefficient of variation. To be certain that fluence level does not affect beam width accuracy, a similar experiment may be performed at low fluence (0.01–0.1 Joules/cm2) on a glass slide coated with commercially available fluorescence coated glass beads. Spot sizes can be measured and statistically analyzed with fluorescence imaging.

The following examples further illustrate, but not limit the operation and application of the present invention.

EXAMPLE 1

Scanning and Separation of Tissue Containing Intimately Associated but Genetically and Histologically Distinct Cell Populations Surgically removed rejected allograft kidneys are infiltrated by large numbers of lymphocytes from the recipient's immune system, so they contain large numbers of cells from two different people in intimate association throughout the tissue.

To discriminate these two cell populations using the laser separation method of this invention, six micron sections of FFPE rejected kidney samples histochemically stained with a combination of monoclonal mouse anti-human leucocyte common antigen (DAKO-LCA) and monoclonal mouse anti-human monocyte/macrophage CD68 (DAKO-CD68) using conditions recommended by the manufacturer. This combination of antibodies detects epitopes in all intact or partially intact lymphocytes contained within the section. Detection is performed with goat anti-mouse secondary antibodies linked to Cy3 (Oncor Image, Inc.), a very stable dye with an excitation and emission spectrum similar to rhodamine. No background staining need be performed, which maximizes the signal to noise ratio in the imaged section. Using this method of staining, it was confirmed that lymphocytes within those rejected kidney sections produce an intense red fluorescent signal on immunostaining by this method. Using the laser separation system configured to detect Cy3, all fluorescent signals in the section can be identified. To effectuate selective ablation of the invading lymphocytes within the sections, the system may be configured to expose the signal producing cell and a 10 um rim around each signal. DNA from one antibody-stained but nonlaser treated section may be included as a control at each locus studied.

DNA is isolated separately from single 6 um hematoxylin and eosin stained sections from rejected transplant kidneys using the method described below in example 3. Amplification of the 115–128 base pair ("bp") microsatellite polymorphism D18S61 is then performed using DNA purified from a section of a rejected transplant kidney. Products are obtained by amplifying DNA from two non-laser dissected rejected kidney sections, and both show 4 separate alleles, consistent with the presence of DNA from two separate individuals. This confirms that two separate genetically distinct cell populations are present in this tissue sample. Amplification of DNA isolated through photodisection of tissue sections of rejected kidney (as described above) will reveal only 2 alleles, demonstrating effective separation of the two distinct, intimately associated cell populations.

EXAMPLE 2

Separation of Tumor Cell in Prostate and Ovarian Biopsies

Histologic sections from frozen prostate cancer biopsies are imaged with light microscopy and noncancerous cells are photoablated using the Brightfield analysis protocol described above. In addition, DNA may be isolated from adjacent non-photodissected sections and from noncancerous tissue from the same patients for comparison. In prostate cancer samples, microsatellite polymorphisms on chromosome 8p22 (currently thought to be the most frequently deleted chromosomal segment in prostate cancer), including D8S261, D8S549, D8S602, and D8S264, for example, as well as LPL on 8p21 may be studied using the method of this invention. In another mode of identification, fluorescent labelled secondary antibodies (such as Cy3 listed above) may be used to detect cells stained with this antibody. The laser ablation system can be configured to ablate cells that do not exhibit these signals. Selectively purified prostate cancer cell RNA and DNA or protein from these sections is then obtained and analyzed.

Ovarian cancer samples also may be analyzed. Histologic sections from papillary serous ovarian carcinomas may be analyzed and photodissected using brightfield microscopy, using the protocol described above. These samples are analyzed for loss of heterozygosity using microsatellite loci on chromosome 17q, which has shown loss of heterozygosity in 70% of primary tumors studied.

EXAMPLE 3

Purification of DNA from Tissue Sections

Sections are transferred to a sterile 1.5 ml eppendorf tube using a sterile blade and deparaffinized with 400 ul xylene for 15 minutes with gentle shaking. The tubes are centrifuged at 10,000×g for 2 minutes and the xylene removed with a sterile pipette. The material is washed three time in 400 ul 100% ethanol. Samples are briefly dried in a vacuum centrifuge until no remaining ethanol is seen. The samples are incubated overnight in 50 ul of a digestion buffer containing 100 mM Tris-HCl, 4 mM EDTA, and 0.5 mg/ml proteinase K, then boiled for 8 minutes to inactivate the enzyme and pulse centrifuged. One microliter of the product is used for the PCR.

PCR reactions and gel electrophoresis may be performed as described in the art (Bova, Cancer Res. 53:3869, 1993). The forward primer is end-labelled for each microsatellite locus to be studied by combining 5.0 ul primer (20 uM), 1.0 ul T4 polynucleotide kinase (10U/ul) (New England Biolabs), 2.0 ul 10× kinase buffer (0.7M Tris HCl 100 mM $MgCl_2$, 50 mM dithiothreitol pH 7.6), 7.0 ul sterile deionized water, and 5.0 ul [gamma$^{-32}$P] dATP and incubating at 37° C. for one hour. After incubation, the T4 kinase is denatured by heating to 68° C. for 20 minutes.

Primer mix is prepared by adding 75 ul sterile deionized water and 5 ul of the reverse primer to the end-labelled forward primer. PCR is performed by combining 1 ul DNA template, 1 ul primer mix, 0.05 ul Taq DNA polymerase (5U/ul) (Boehringer-Mannheim), 1.2 ul 10×PCR buffer (100 mM Tris-HCl, 15 mM $MgCl_2$, 500 mM KCl, pH 8.3) (Boehringer-Mannheim), 1.2 ul dNTP mix (equal volumes of dATP, dCTP, dGTP, and dTTP each at 10 mM), and 7.6 ul sterile water per reaction. The mix is prepared on ice, mixed well, and covered with one drop mineral oil. The PCR tubes are preheated to 94° C. prior to placing the reaction tubes or plates onto the pre-heated (94° C.) thermocycler (Hybaid Omnigene). After 2 minutes at 94° C., 28 cycles of denaturation at 94° C.×60 seconds, annealing at 60° C. (D8S261, D2S123) or 55° C. (D18S61, D17S798)×30 seconds, and extension at 72° C.×30 seconds, with 2 seconds extension/cycle are performed. The products are mixed with 12 ul of stop buffer containing 95% formamide, 0.05% xylene cyanol, 0.05% Bromphenol blue, and 20 mM EDTA. Samples are heated to 94° C. for 3 minutes, then placed on ice, and loaded by 1 ul aliquots onto 6% acrylamide sequencing gels containing 8.0 M Urea. Gels are run for 1.5–3 hours depending on product size. The gels are vacuum dried and exposed to Kodak Biomax film at room temperature or −70° C. depending on intensity of the signal detected by geiger counter.

Using the apparatus and method of the present invention, the user can select specific regions of the tissue section to be preserved. The device will automatically ablate nonselected portions of the section, while selected cells' DNA or RNA will remain intact for subsequent analysis by PCR or other genetic methods. By providing convenient laser purification of tumor cells from tissue sections, the method and apparatus of the present invention will facilitate genetic research in cancer, and will provide a tool for the accurate molecular diagnosis of tumors.

The present invention overcomes prior limitations by employing direct vision video analysis of tissue sections integrated with a UV laser and improved tissue handling techniques whereby the user can efficiently obtain samples of tumor DNA or RNA of high purity, while at the same time obtaining important histological information about the tissue. By specially configuring a standard microscope and stage motion system, a computer, a compact, economical laser, and specialized software, this system will enhance pathologic practice and speed cancer research. Indeed, the present invention permits the examination, selection and destruction of the DNA, RNA or protein of individual cells with heretofore unobtainable accuracy, simplicity and efficiency.

Since many modifications, variations and changes in detail may be made to the described embodiments, it is intended that all matter in the foregoing description and shown in the accompanying drawings be interpreted as illustrative and not in a limiting sense.

I claim:

1. A method for purifying a heterogenous cell population in a tissue section, said method comprising:
    (a) supporting a tissue section having a heterogenous population of cells on a tissue support under a microscope with an objective for viewing said tissue section;
    (b) scanning said tissue section with a video camera and producing a mosaic of video images representing the tissue section;
    (c) displaying said mosaic of video images representing the tissue section;
    (d) analyzing each frame of said mosaic of video images based upon target cell selection criteria and selecting target cells of interest based upon said target cell selection criteria; and
    (e) automatically and selectively ablating each selected target cell utilizing a radiant energy beam.

2. The method of claim 1 further comprising the step of automatically analyzing each frame of said mosaic of video images based upon target cell selection criteria and automatically selecting target cells of interest based upon said target cell selection criteria.

3. The method of claim 1 further comprising the step of visually analyzing each frame of said mosaic of video images based upon target cell selection criteria and manually selecting target cells of interest based upon said target cell selection criteria.

4. The method of claim 2 further comprising the steps of manually selecting additional target cells of interest or manually deselecting target cells automatically selected based on said target cell selection criteria.

5. The method of claim 1 further comprising the steps of:
    (a) changing the magnification of said microscope to a higher magnification; and
    (b) repeating steps (a) through (e) in claim 10.

6. The method of claim 1 wherein the step of automatically and selectively ablating each selected target cell produces a tissue section having relatively intact DNA, RNA or protein from only the non-selected cells.

7. A method for laser-treating specific target cells in a tissue section having a heterogenous population of cells, comprising:
    (a) supporting said tissue section on a tissue support under a microscope with an objective for viewing said tissue section;
    (b) scanning said tissue section with a video camera to produce a mosaic of video images representing said tissue section;
    (c) optionally displaying said mosaic of video images;
    (d) analyzing said mosaic of video images based upon preselected target cell selection criteria;
    (e) selecting said specific target cells based upon predetermined target cell selection criteria; and
    (f) laser-treating said selected target cells.

8. A method according to claim 7, wherein said analysis and selection are performed automatically by a computer.

* * * * *